United States Patent [19]

Cooney et al.

[11] 4,198,979
[45] Apr. 22, 1980

[54] URINE COLLECTOR FOR WOMEN

[75] Inventors: Patricia A. Cooney, Hicksville; Donald G. Cooney, West Islip, both of N.Y.

[73] Assignee: Cooney Catheter Corporation, West Babylon, N.Y.

[21] Appl. No.: 807,430

[22] Filed: Jun. 17, 1977

[51] Int. Cl.² ............................................. A61F 5/44
[52] U.S. Cl. ................................................ 128/295
[58] Field of Search .............. 128/275, 295, 294, 283, 128/2 F; 4/113.1, 114.1, 144.1

[56] References Cited

U.S. PATENT DOCUMENTS

| | | | |
|---|---|---|---|
| 1,696,763 | 12/1928 | Hare | 128/283 UX |
| 2,448,938 | 9/1948 | Wayne | 128/294 |
| 3,194,238 | 7/1965 | Breece, Jr. | 128/295 |
| 3,312,221 | 4/1967 | Overment | 128/275 |
| 3,661,155 | 5/1972 | Lindan | 128/295 |
| 3,722,503 | 3/1973 | Hovick | 128/2 F |
| 3,963,020 | 6/1976 | Hall | 128/295 |

FOREIGN PATENT DOCUMENTS 1559275  1/1969  France ............................ 128/295

Primary Examiner—Robert W. Michell
Assistant Examiner—C. W. Shedd
Attorney, Agent, or Firm—Robert A. Kelly

[57] ABSTRACT

A urine collection device for women comprising a one piece generally funnel shaped rigid collection means having a flanged wide orifice which orifice has flanged lip on the upper side thereof forming a seat thereon; sealant composed of a layer of a double adhesive faced layer of body adhesive mounted in the seat; the upper surface of the flanged wide orifice containing the sealant being shaped to fit within the contours of the permineum cavity with the external urethral orifice of the wearer being in alignment with the wide orifice of the collector and the sealant means being in contact with the vestibular tissue to prevent substantial leakage of material from between the tissue and the sealant. In a preferred embodiment of the urine collector a pommel formed by the lip and rising away from the collection to enhance positional stability, alignment and further prevent leakage. The whole orifice can cover both the urethral and vaginal orifices to collect discharges therefrom. Conventional liquid reservoirs can be employed to store the collected discharges.

8 Claims, 9 Drawing Figures

URINE COLLECTOR FOR WOMEN

BACKGROUND OF THE INVENTION

1. Field of the Invention

The invention relates to a device which can be affixed on the body of a woman for continuously collecting urine both in the case of bedridden women and active women who are either continent or incontinent. More specifically the invention relates to a device which will alleviate the need for diapers and/or internal catheraters being worn by women with a problem of incontinence.

2. Description of the Prior Art

A variety of intravaginal urinals are known which are designed to be worn by the female for long periods of time and are designed for bedridden incontinent or otherwise incapacitated women. These devices usually have a member which is inserted between the labia minora of the user to rest flush up against the vestibule of user with an orifice of the device encompassing the external urethral orifice of the user and which may or may not have an anchoring post for anchoring the device to the vaginal passageway to prevent displacement of the alignment of the external urethral orifice and the orifice of the collector. They rely upon elastic straps to force the rigid surface of device to be tightly pressed against the body of the wearer to prevent leakage or seepage in all positions, sitting, lying or standing. Serious problems arise when such devices are used because of chaffing resulting from movement between the body surface of the wearer and the device. A high degree of pressurized contact of the device against the body to prevent leakage must be employed which causes the chaffing. Some in the art have even resorted to using a pitted surface on the device in an attempt to decrease the amount of pressure to form a seal but such a surface inherently increases the opportunity for abrasion.

To eliminate the problems which result from prior external collector means, hospitals and nursing homes still resort to internal catherization or diapering of incontinent patients and this results in both vastly decreased mobility of the patient which further debilitates the patient and to a very great risk of internal bladder and urethral infections. The use of diapers is a major cause of ulceration for patients.

The magnitude of the problem is clearly illustrated by the fact that surveys show that 40 percent of all hospitals acquired infections occur in the urinary track and that 75 percent of these are most often caused by the indwelling catheter. Other studies have shown that each decubitis ulcer increases the cost of medical for the unfortunate individual and when it occurs by thousands of dollars and that incontinence in the form of urine reduces the resistance of the skin to other physical factors and increases the risk of necrosis and decubitis ulceration.

SUMMARY OF THE INVENTION

This invention discloses a generally funnel shaped urine collection means capable of use by both mobile and immobile women to collect urine exiting from the external urethral orifice which is aligned with the wide end of the collection means. There is provided a flanged lip forming a seat around the wider orifice of the collection means shaped so that outer surface of the flanged lip when covered with a sealant means such as a layer of body adhesive can be snugly placed against the vestibule of a wearer and at least a portion of the inner surface of the flanged lip will be covered by the labia minora of the wearer to permit its normal pressure to urge the collection means against the vestibule. The outer surface of the lip is coated with a sealant means such as a commercially available body adhesive to provide a seal between the lip surface and the vestibule both to prevent leakage and to assist in preventing the collection means from being moved out of position. In a preferred embodiment of the invention a portion of the normally substantially flat surface of the flanged lip of the collection means is warped upwardly away from the outer surface of the lip to form a pommel which is insertible into the vaginal orifice of a wearer to both prevent backward movement of the collector and to assist in the channeling of urine from users of the device whose external urethral orifice has become misaligned with the vaginal channel. Further there is provision for the coupling of reservoir for storing quantities of urine coupled to the narrow end of the collection means and harness means for supporting both the collector means and the reservoir means.

It is an object of this invention to provide a substantially leakproof device for collecting urine from women which is economical and sanitary.

It is a further object of this invention to provide an external, efficient, sanitary, economical device for collecting urine from women over protracted periods which does not limit the mobility of the wearer.

It is a further object of this invention to provide an external urine collector which will collect both urine and vaginal discharge from women.

Additional objects will be evident from the description of the drawings and preferred embodiments described below.

DESCRIPTION OF THE PREFERRED EMBODIMENT

Figure 1:
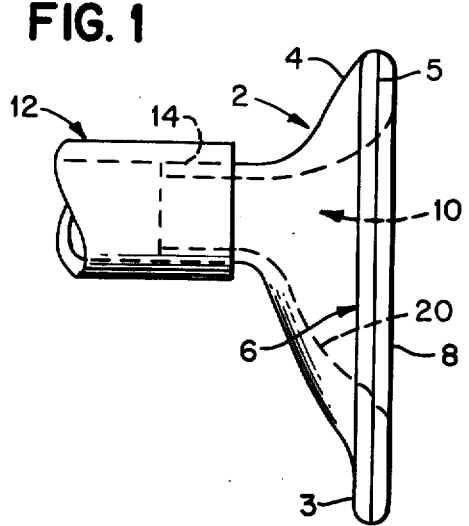
FIG. 1 is a side elevation showing the funnel shaped collection means with a tube attached to the collection means.

The collection means is generally designated 2 in FIG. 1. It is a one piece generally rigid funnel shaped collection means 2 molded of thermosetting plastic and the like.

The collection means 2 has a wide orifice 10 which is a generally elliptically shaped opening and a narrow tubular orifice 14 at the opposite end of the collection means 2. The wide orifice 10 of the collection means 2 has a flanged means 6 surrounding it. Flanged means 6 having a seat 5 with upper surface 4 and underside surface 3. The upper surface 4 of seat 5 has affixed thereto a sealant means 8 consisting of a layer of body adhesive. Seat 5 surrounding orifice 10 is shaped and sized so that the upper surface 4 thereof which is covered with sealant 8 will be capable of being placed snugly against the vestibular tissue of a woman so that orifice 10 will cover the external urethral orifice of a wearer of the collection means; with the labia minora of the wearer contacting the underside 3 of seat 5 in a relationship whereby the labia minora urges the upper surface 4 of seat 5 having sealant 8 thereon into more intimate contact with the vestibule of the wearer.

The normal location of the external urethral orifice which is generally located approximately midway between the external vaginal orifice and the clitoris. A problem sometimes arises with women who have given birth to many children and/or had a vigorous sex life. The problem is that the external urethral orifice is shifted to a position which is too close to the vaginal opening so that the upper surface 4 of seat 5 having sealant means 8 thereon cannot be brought to bear against a sufficient surface area of the vestibule or tissue; indeed in many cases the external orifice sometimes can empty into the vaginal tract. In such cases if a collection means 2 shaped as shown in FIG. 1 is desired to be used it is advised that it be so sized and shaped that the seat 5 having sealant means 8 thereon surrounds both the external urethral orifice and the vaginal orifice.

Figure 3:
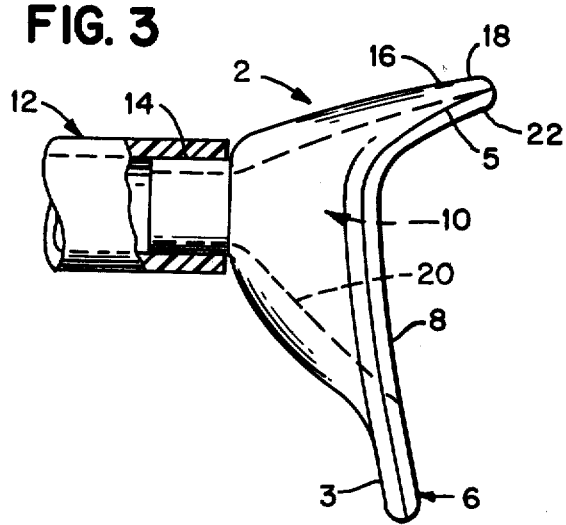
FIG. 3 is a partial section of a side elevation of a collection means having a tube attached to the collection means wherein the collection means has a pommel.

In a preferred embodiment of the invention as shown in FIG. 3 the collection means 2 has a seat 5 which also forms a pommel 16 which is insertable into a portion of the vagina wherein the interior surface 3 forms a contact surface 18 on the pommel 16 of seat 5 which surface 18 is shaped to rest against the backwall of the vaginal passage, and to permit egress of fluid material from the external vaginal orifice and the external urethral orifice through orifice 10 into the interior of collection means 2. Preferentially the entire surface of pommel 16 is coated with sealant 8 so that a continuous seal is provided for orifice 10 between the collection means 2 and the body of the wearer thereof.

The generally funnel shaped collection means of this invention having wide orifice 10 has a narrow tubular shape orifice 14 at the end of the collection means 2 opposite orifice 10 is adapted to be coupled with tube means 12.

Figure 2:
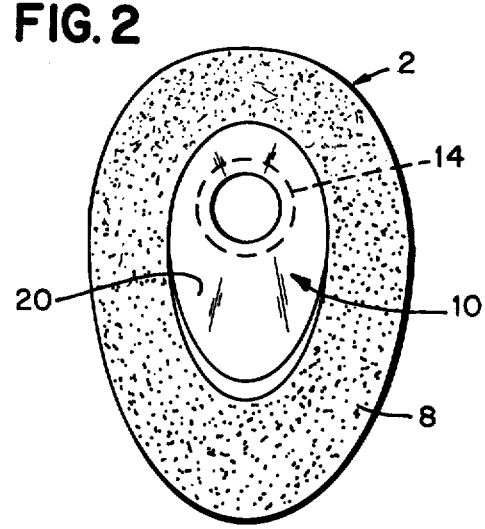
FIG. 2 is a rear elevation of the collection means.
Figure 4:
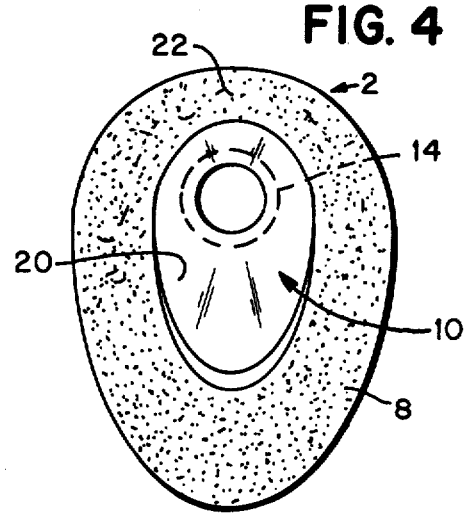
FIG. 4 is a rear elevation of FIG. 3.
Figure 6:
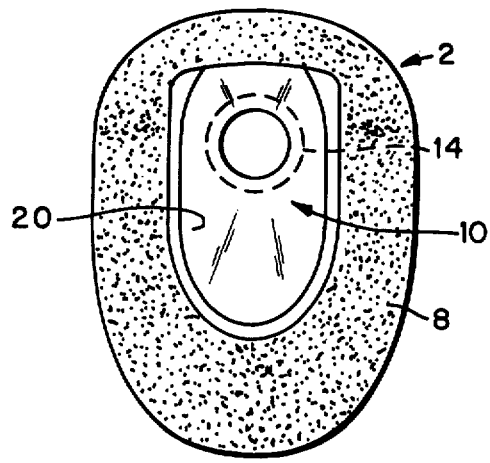
FIG. 6 is a rear elevation of FIG. 5.

By the term generally funnel shaped collection means 2 is meant that the walls 20 of the collection means 2 extending from orifice 10 curve taper inwardly to form a generally circular narrow tubular shaped orifice but the shape of orifice 10 is generally elliptical when viewed from a rear elevation as shown in FIG. 2, FIG. 4 and FIG. 6.

Of course the particular geometric shape of both the orifice 10 and the collection means 2 is not a limitation on this invention. For example, orifice 10 can be circular or oval shaped, the slope of walls 20 can be uniform or varied, etc.

Figure 8:
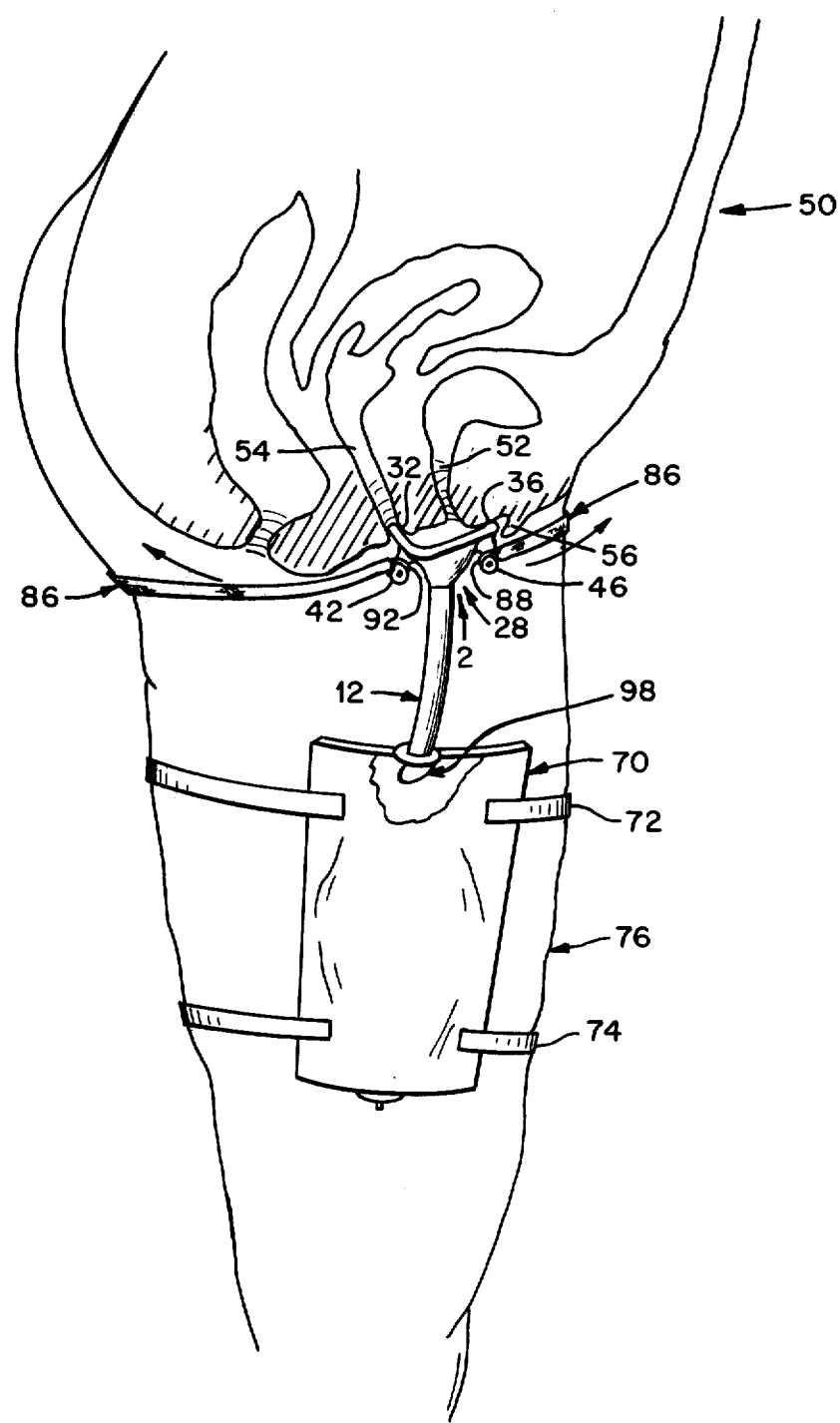
FIG. 8 is partially crossectional view of a wearer of the collector shown in FIG. 5 with a reservoir attached thereto in its operative state.

The collection means 2 as shown in FIG. 6 has arms 42 and 44 extending from the exterior walls 20 of the collection means 2. There is a recess 45 in arm 46 and a recess 40 in arm 42 to enable the ring of a holding strap 86 (as shown in FIG. 8) to be held into position on both arm 42 and arm 46. Further arm 42 and arm 46 can be respectively provided with orifices 44 and 48 to enable a more secure attachment of straps thereto.

Figure 5:
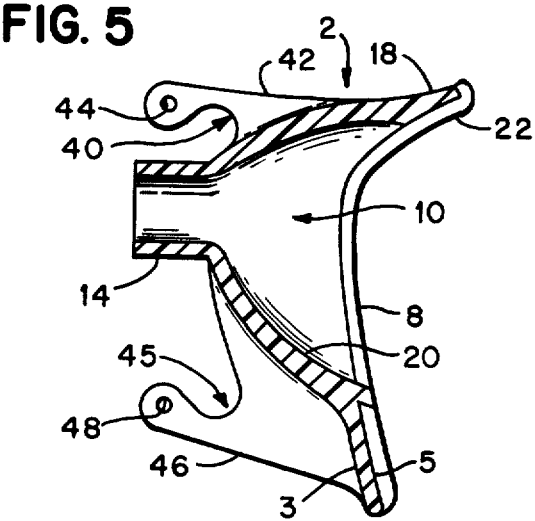
FIG. 5 is a sectional side elevation of a collection means having a pommel and two extending arms with locking means recess.
Figure 7:
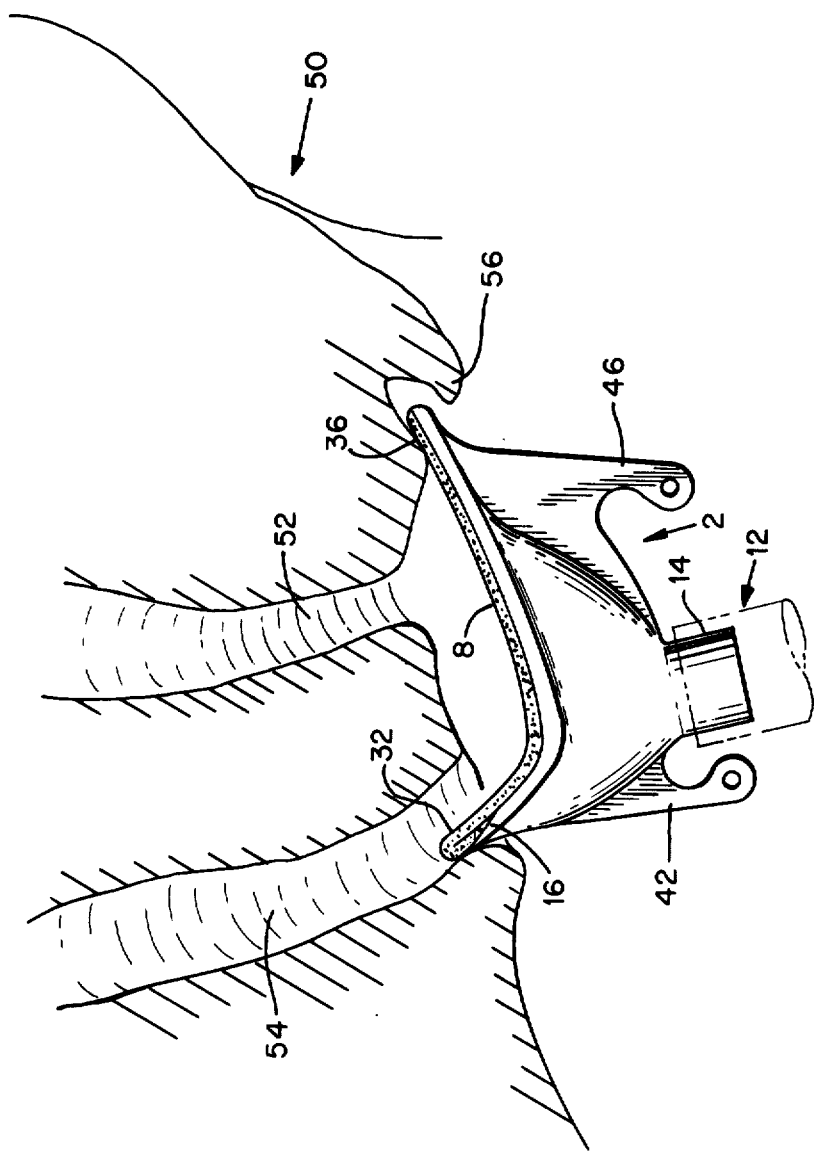
FIG. 7 is an exploded partially crossectional view of a wearer of the collector shown in FIG. 5.

FIG. 7 showing an exploded partially crossectional view of a wearer of the collection means generally shown in FIG. 5. In this figure the pommel 16 is shown in contact with the posterior wall of the vaginal tract 54 and with the opposite side seat 5 being in contact with the vestibule of the wearer and having the external urethral opening 52 in contact with interior portion of collection means 2 through orifice 10 thereof. Not shown but of course necessary for the proper operation of the collection means 2 is that the sealant 8 coated seat impinges upon the body surface of the wearer 50, with the sealant means 8 forming a circumferential seal between the collection means 2 and the vestibular tissue, thus directing the flow of material from the urethra and the vagina through collection means 2 into tube means 12.

FIG. 8 is a partially crossectional view of a wearer 50 of the collection means 2 similar to that shown in FIG. 7 wherein reservoir means 70 is operably connected to tube 12 which in turn is operably connected to collection means 2. Discharges from the urethra 52 and vagina 54 of wearer 50 are collected and passed through collection means 2 and thereafter passed through tube means 12 into reservoir means 70. Straps 72 and 74 are operably connected both to reservoir means 70 and the thigh 76 of the wearer 50, to provide support for reservoir means 70 and to prevent it from adding pressure on collection means 2 to dislodge it from the body of wearer 50.

Figure 9:
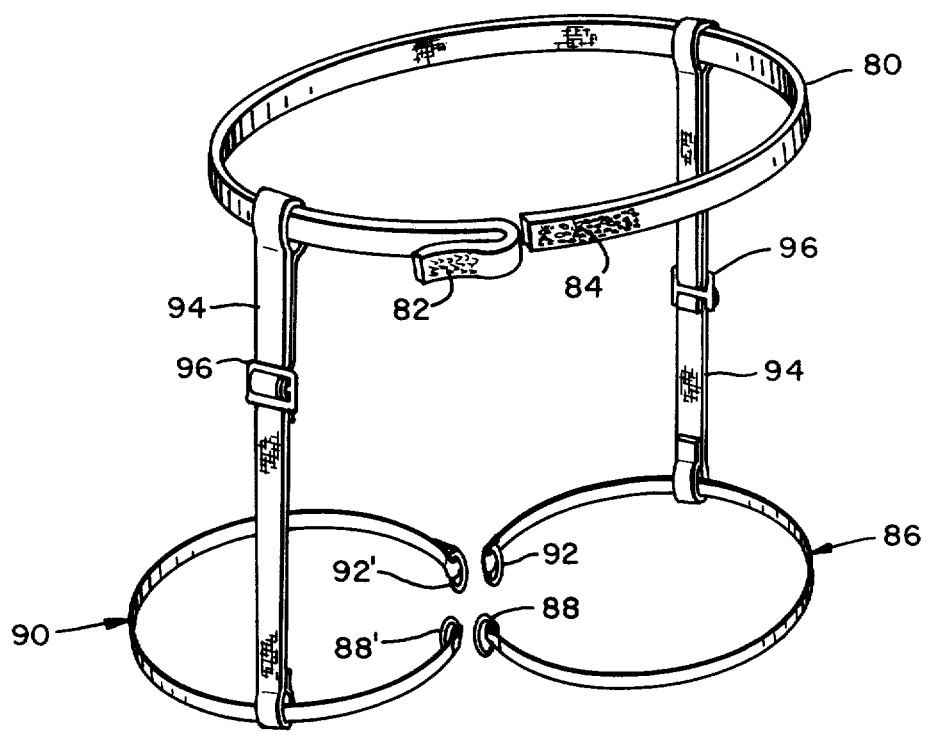
FIG. 9 is a holding harness with adjustable length longitudinal adjustable straps having waist and leg bands attached hereto with fastening means on the leg bands for attaching the harness to the collection means of FIG. 5.

FIG. 9 illustrates a harness device having waist band 80 having a Velcro-brand type closure having a male flap 82 and a female flap for adjustable length contact closure of the waistband 80. Straps 96 affixed to and depending from waistband 80. Each strap 90 having individual length adjustment means 96 on each strap. Leg straps 90 and 86 are shown to be moveably mounted on straps 96 and the end of each strap has a ring 92', 88', 92 and 88 which are adopted to be affixed to the arms shown on the collection means 2 as shown in FIG. 8 hereof. The harness means shown in FIG. 9 is not necessary for the successful use of this invention. They are utilized merely to provide additional security to user of this invention when the user is vigorously ambulatory such as walking, jogging, playing tennis, etc.; to prevent accidental dislodgement of the urine collection means 2 by virtue of body motions. When a harness is used care should be taken to provide sufficient slack in the straps 86, 90 and 94 so that the collection means 2 is not unduly pressured to impinge against the body of a wearer therrof to cause sores resulting from abrasion and pressure.

Any type of container for holding liquids can be employed in the use of the invention disclosed herein. The reservoir means 70 shown in FIG. 8 hereof is suitable for use by an active ambulatory user and should have a valve 98 to prevent backflow of urine out reservoir means 70. Such reservoir means are currently available in most drugstores. Tube means 12 could be allowed to drain into any suitable container for liquids such as a pail, etc. in non ambulatory patients.

The urine collection means 2 can be made of any biomedical grade plastic such as silicone and the like. It should be shaped to fit within the contours of the perineum vestibule since this shape permits the most adhesion between the sealant means and the body tissue of the wearer. The provision of the pommel 12 as shown in FIG. 3 not only restricts movements of the device, it also orients the device for and upon installation and prevents leakage posteriorly.

The sealant means 8 is a layer of body adhesive which adhesives are well known in the art. These body adhesives generally are made of a mixture of gelatin, pectin, sodium carborymethylcellulose and polycarbons such as polyisobutylene. They are available commercially in the form of deformable sheets having the consistency of thick putty. A layer of this sheet material is layed on the upper surface 4 of the flanged means 6 of the collection means 2 and the sealant means is then brought in contact with the outer surface of the tissue of the wearer of the device. It is to be understood that such body adhesives do not form a permanent type bond onto the surface of the wearer but interact with the natural substances on the interior of the permineum vestibule and form a viscous pliant seal therewith. Of course the sealant means should not be allowed to block the orifice 10 of the collection means 2.

Typical of the class of body adhesives found usable in our invention are those disclosed in U.S. Pat. No. 3,339,546 issued to James Ling Chen on Sept. 5, 1967.

The body adhesives available and sold under the trademark Stomahesive (E. R. Squibb and Sons, Inc., Princeton, New Jersey) and Stomagard (Dard Laboratories, Inc., St. Louis, Missouri) have been found to be usable as sealant means in the practice of our invention. The sealant means should be selected primarily for its ability to form a substantially leak proof seal between the body of the wearer and the device and for its compatability with the health of the patient and not for the degree of adhesion that can be achieved. Those skilled in the art will know which products can be used and if it is desired to use other adhesives than those given herein to form the sealant means, then tests and care should be taken to ensure that the adhesive chosen does not produce adverse effects such as abrasion, ulceration and the like.

To install the device of this invention the perineum should be cleaned thoroughly, the sealant means 8 could be moistened and the curved edge of the pommel 16 having the sealant means 8 thereon should be fitted securely into the vaginal orifice at the same time placing the seat 5 having sealant means 8 thereon snugly against the vestibular tissue between the labia minora; thereafter, the labia minora should be allowed to contact the underside 3 of the flanged means 6. Prior to application of the devices of this invention a patch test of the particular sealant means should be performed. This can be accomplished simply by placing a small piece of the body adhesive to be tested on the inner aspects of the arm, cover with tape and remove after 48 hours and observe for adverse reactions.

Traditional skin barriers (i.e. zinc oxide ointment, Desitin ointment, petroleum jelly, etc.) may be used for patients who are sensitive to adhesives or prone to breakdown (i.e. dehydration, diabetics, fair skinned, etc.). However the use of such barriers may decrease sealing properties and should be avoided if possible. The device can be removed after 8 hours to permit washing with mild soap and water.

The body adhesives usable in this invention have adhesive (sticky) layers on both sides thereof.

A device constructed in accordance with this invention substantially shown in FIG. 9 was worn by a woman for a period of 48 hours in which the wearer played tennis, shopped, slept and otherwise led a normal life excepting for the wearing of the device without leakage from the system.

It is to be understood that the drawings and descriptive matter are in all cases to be interpreted as merely illustrative of the principles of the invention, rather than as limiting the same in any way, since it is contemplated that various changes can be made in various elements to achieve like results without departing from the spirit of the invention or the scope of the appended claims.

What is claimed is:

1. A urine collection device for women comprising:
   a one piece generally funnel shaped rigid collection means having a flanged wide orifice which orifice has a flanged lip on the upper side thereof forming a seat thereon;
   sealant means composed of a layer of body adhesive having adhesive on both sides of said layer mounted in the seat;
   the upper surface of the flanged wide orifice containing the sealant means being shaped to fit within the contours of the perineum cavity with the external urethral orifice of the wearer being in alignment with the wide orifice of the collection means and the sealant means being in contact with the vestibular tissue;
   a narrow orifice located in opposition to said flanged wide orifice to permit urine to be removed from the funnel shaped rigid collection means;
   said flanged wide orifice being capable of encompassing both the urethral orifice and the vaginal orifice of a wearer of the device;
   said narrow orifice being operably connected by tubing means to reservoir means for storing urine;
   said flanged lip being so shaped that the inner surface of the labia minora of a wearer thereof are brought in contact with the underside of the flanged lip in a relationship which presses the flanged lip having sealant means thereon against the vestibular tissue of the wearer;
   said sealant means being capable of forming a pliant viscous seal between the flanged lip and the vestibular tissue of the wearer to prevent liquids from escaping between the flanged lip and the vestibular tissue.

2. The urine collection device of claim 1 wherein said reservoir means contains valve means to prevent the flow of urine from said reservoir means back through said tubing means.

3. The urine collection device of claim 2 wherein a first harness means is provided to support and mount said reservoir means onto the body of the woman wearing the urine collection device.

4. The urine collection device of claim 3 wherein a second harness means is provided and affixed to said urine collection means to maintain it in position with respect to the body of a wearer of the urine collection device.

5. A urine collection device for women comprising:
   a one piece generally funnel shaped rigid collection means having a flanged wide orifice which orifice has flanged lip on the upper side thereof forming a seat thereon, said flanged lip being so shaped that the inner surface of the labia minora of a wearer thereof are brought in contact with the underside of the flanged lip in a relationship which presses the flanged lip having sealant means thereon against the vestibular tissue of the wearer;

a pommel formed by a portion of said flanged lip having said seat rising from said seat shaped for insertion into the vaginal orifice;

sealant means composed of a layer of body adhesive having adhesive on both sides of said layer mounted in the seat, and covering all sides of said pommel, said pommel covered with said sealant means being shaped to rest against the posterior wall of the vagina to permit the flow of liquids into the interior of said collection device from both the urethra and the vagina and said sealant means being capable of forming a circumferential pliant viscous seal formed by the sealant means between the vestibular tissue of the wearer and the orifice of the collection means;

the upper surface of the flanged wide orifice containing the sealant means being shaped to fit within the contours of the perineum cavity with the external urethral orifice of the wearer being in alignment with the wide orifice of the collection means and the sealant means being in contact with the vestibular tissue;

a narrow orifice located in opposition to said flanged wide orifice to permit urine to be removed from the funnel shaped rigid collection means;

said flanged wide orifice being capable of encompassing both the urethral orifice and the vaginal orifice of a wearer of the device;

said narrow orifice being operably connected by tubing means to reservoir means for storing urine.

6. The urine collection device of claim 5 wherein said reservoir means contains valve means to prevent the flow of urine from said reservoir means back through said tubing means.

7. The urine collection device of calim 6 wherein a first harness means is provided to support and mount said reservoir means onto the body of the woman wearing the urine collection device.

8. The urine collection device of claim 7 wherein a second harness means is provided and affixed to said urine collection means to maintain it in position with respect to the body of a wearer of the urine collection device.

* * * * *